(12) United States Patent
Koh

(10) Patent No.: US 7,308,309 B1
(45) Date of Patent: Dec. 11, 2007

(54) DIAGNOSING CARDIAC HEALTH UTILIZING PARAMETER TREND ANALYSIS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 278 days.

(21) Appl. No.: 11/032,639

(22) Filed: Jan. 11, 2005

(51) Int. Cl.
*A61N 1/365* (2006.01)
*A61B 5/0245* (2006.01)
*A61B 5/021* (2006.01)
*A61B 5/0402* (2006.01)
*A61B 5/08* (2006.01)

(52) U.S. Cl. .................. 607/17; 600/481; 600/508; 600/509; 600/529

(58) Field of Classification Search ............... None
See application file for complete search history.

(56) References Cited

U.S. PATENT DOCUMENTS

| | | | | |
|---|---|---|---|---|
| 4,986,277 | A | 1/1991 | Sackner .................. | 128/672 |
| 5,146,414 | A | 9/1992 | McKown et al. .......... | 364/510 |
| 5,372,607 | A | 12/1994 | Stone et al. .............. | 607/30 |
| 5,476,483 | A | 12/1995 | Bornzin et al. ........... | 607/17 |
| 5,482,035 | A * | 1/1996 | Paloheimo ............... | 600/310 |
| 6,024,705 | A * | 2/2000 | Schlager et al. .......... | 600/508 |
| 6,299,582 | B1 | 10/2001 | Brockway et al. ........ | 600/484 |
| 6,366,812 | B1 | 4/2002 | Levine et al. ............. | 607/27 |
| 6,394,958 | B1 | 5/2002 | Bratteli et al. ............ | 600/485 |
| 6,466,819 | B1 * | 10/2002 | Weiss ...................... | 607/5 |
| 6,506,161 | B2 | 1/2003 | Brockway et al. ........ | 600/484 |
| 6,572,557 | B2 | 6/2003 | Tchou et al. .............. | 600/483 |
| 6,647,293 | B2 * | 11/2003 | Meyer ..................... | 607/5 |
| 6,675,043 | B1 * | 1/2004 | Prutchi et al. ............ | 607/17 |
| 6,689,069 | B2 | 2/2004 | Bratteli et al. ............ | 600/485 |
| 2001/0037067 | A1 * | 11/2001 | Tchou et al. .............. | 600/483 |
| 2003/0093125 | A1 * | 5/2003 | Zhu et al. ................. | 607/25 |
| 2004/0167411 | A1 | 8/2004 | Kolluri et al. ............. | 600/490 |
| 2004/0220632 | A1 * | 11/2004 | Burnes ..................... | 607/9 |
| 2005/0080460 | A1 * | 4/2005 | Wang et al. .............. | 607/17 |

FOREIGN PATENT DOCUMENTS

WO WO 03/077755 9/2003
WO WO 2004/012597 A1 2/2004

OTHER PUBLICATIONS

Charbonnier, Sylvie, et al., "On-Line Segmentation Algorithm for Continuously Monitored Data in Intensive Care Units," *IEEE Transactions on Biomedical* Engineering, Mar. 2004, vol. 51, No. 3: pp. 484-492.

* cited by examiner

*Primary Examiner*—Kristen Droesch Mullen

(57) ABSTRACT

Diagnosing a patient's cardiac health through the use of parameter change analysis involves a system that includes an implantable cardiac device to sense a parameter related to a patient's heart. The system further includes a parameter change detection sub-system configured to derive a trend of the parameter over time and to detect changes to the trend. The trend and detected changes can then be used to diagnose changes in the patient's cardiac health. Results of the diagnosis are stored and presented to a care physician.

22 Claims, 10 Drawing Sheets

DIAGNOSING CARDIAC HEALTH UTILIZING PARAMETER TREND ANALYSIS

FIELD OF THE INVENTION

The present invention generally relates to implantable devices and diagnostic systems for diagnosing a patient's cardiac health.

BACKGROUND

Heart failure is a condition in which the heart is unable to pump enough blood to sustain normal bodily functions. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Implantable cardiac devices, such as pacemakers and defibrillators, monitor many different cardiac parameters that may be used to determine how well a patient's heart is functioning. For instance, implantable cardiac devices can measure morphology-related parameters, impedance, intrinsic heart rate, heart rate recovery, heart rate variability, conduction delay, pressure, posture, activity, and so forth. Each of these parameters can be used to evaluate the patient's heart.

The implantable cardiac devices are commonly configured to stimulate the heart with pulses in response to individual or combinations of these measured parameters. Additionally, the devices can store these parameters over time and periodically transmit the parameters to external diagnostic systems for more exhaustive analysis.

Unfortunately, as physicians, clinicians, and other care providers become increasingly busier with more patients to examine and less time to spend with each patient, it is often difficult to diagnose whether a patient's cardiac health is improving or deteriorating based on a cursory review of the many raw parameters collected by the implantable devices. Accordingly, there is a need to summarize the individual parameters in a way that assists the care provider quickly diagnose the patient's cardiac health. This would be particularly helpful for quickly identifying those patients whose conditions have degenerated to a point of requiring immediate attention.

SUMMARY

Diagnosing a patient's cardiac health through the use of parameter change analysis is described. One system includes an implantable cardiac device to sense a parameter related to a patient's heart. The system further includes a parameter change detection sub-system configured to derive a trend of the parameter over time and to detect changes to the trend. The trend and detected changes can then be used to diagnose changes in the patient's cardiac health. Results of the diagnosis are stored and presented to a care physician.

DETAILED DESCRIPTION

Overview

The following discussion describes techniques for diagnosing a patient's cardiac health by deriving a trend in one or more heart-related parameters over time and detecting a change in the trend.

For discussion purposes, the techniques are described in the context of diagnosing heart conditions that might suggest a potential for heart failure. Some parameters are measured using an implantable cardiac device while other parameters may be collected by other means. Processing of the parameters can be implemented within the implantable device (assuming it is configured with sufficient memory and processing capabilities) or alternatively at an external device, such as a programmer or diagnostic computing system.

In described implementations, a parameter change sub-system utilizes a line segment algorithm to evaluate heart-related data. The line segment algorithm, among other attributes, evaluates the heart-related data over time to identify a trend change in that data. As additional data is analyzed or becomes available, the algorithm determines whether the existing trend is continuing or whether a meaningful change in the trend is occurring. If confirmed, the trend change suggests that the existing trend has ended and a new trend has begun.

The trend change information is provided or graphically presented to the patient's clinician. The clinician can then make a more informed decision as to how to treat the patient, including weighing such factors as whether to prescribe a new therapy or alter an existing one.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes. The following discussion describes an exemplary implantable cardiac device and diagnostic system that implements a parameter change sub-system.

Implantable Cardiac System

Figure 1:
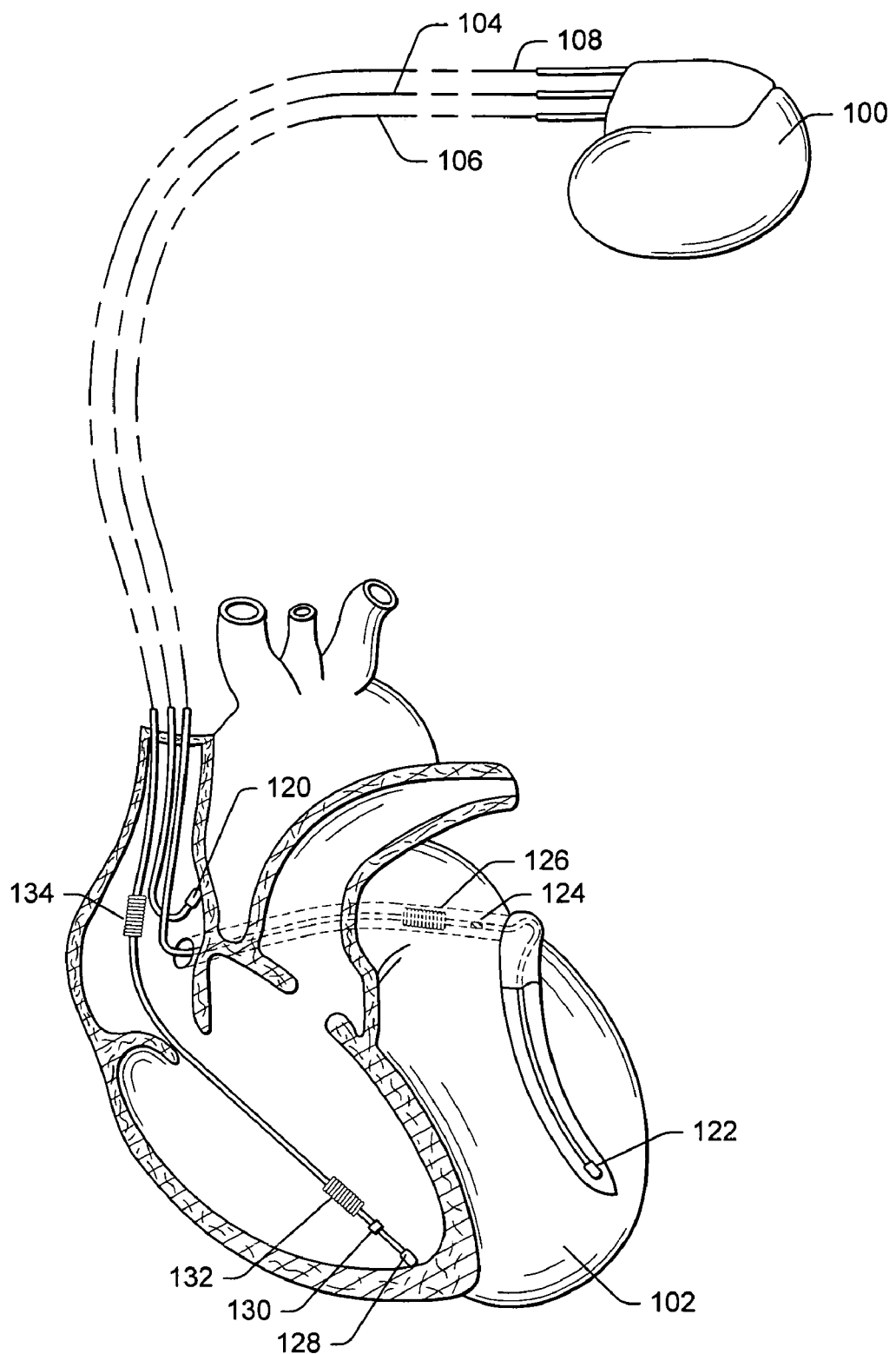
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
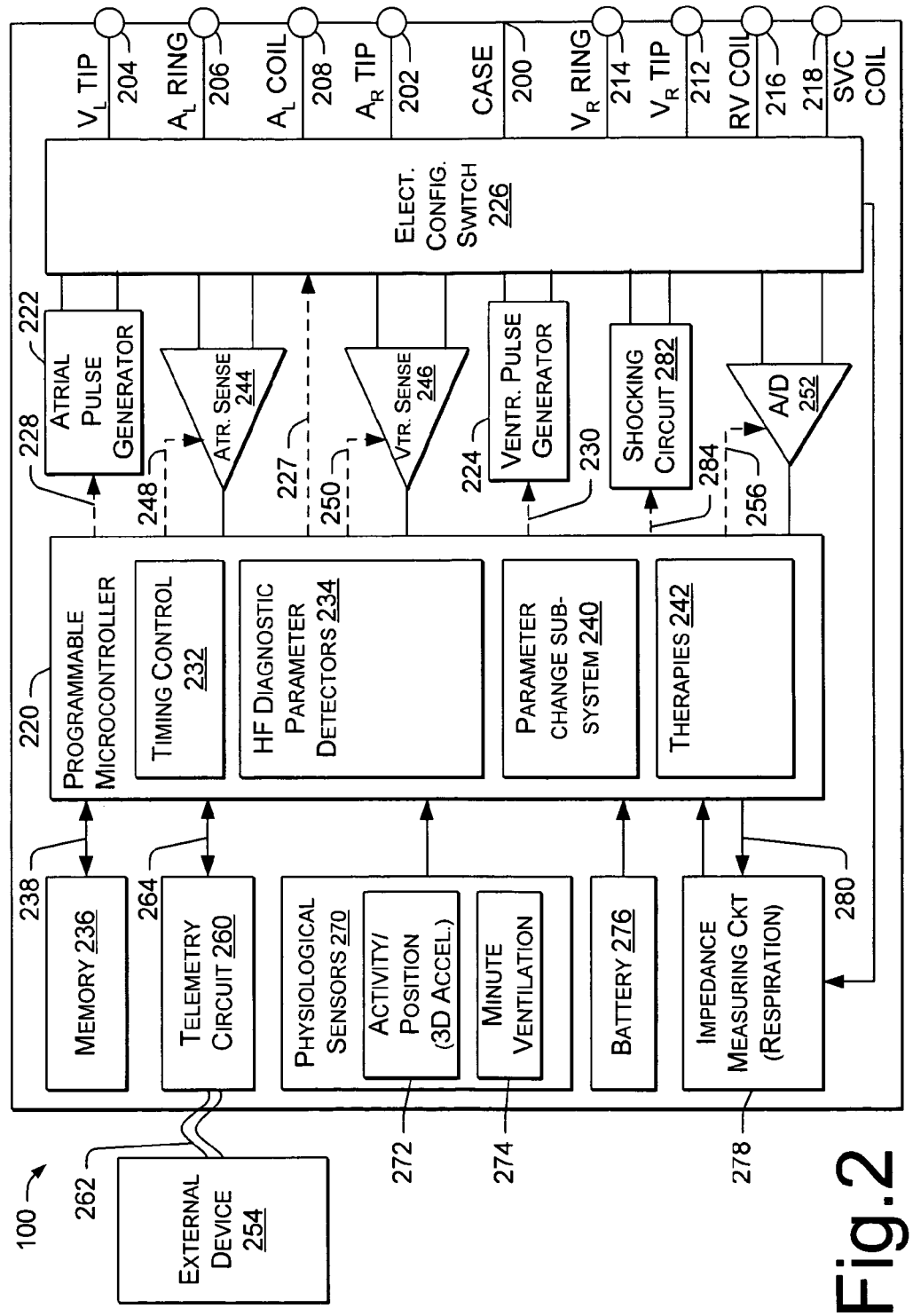
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

- a right atrial tip terminal (AR TIP) 202 for atrial tip electrode 120;
- a left ventricular tip terminal (VL TIP) 204 for left ventricular tip electrode 122;
- a left atrial ring terminal (AL RING) 206 for left atrial ring electrode 124;
- a left atrial shocking terminal (AL COIL) 208 for left atrial coil electrode 126;
- a right ventricular tip terminal (VR TIP) 212 for right ventricular tip electrode 128;
- a right ventricular ring terminal (VR RING) 214 for right ventricular ring electrode 130;
- a right ventricular shocking terminal (RV COIL) 216 for RV coil electrode 132; and
- an SVC shocking terminal (SVC COIL) 218 for SVC coil electrode 134.

The implantable cardiac device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on.

Microcontroller 220 is also equipped with multiple detectors 234 used to detect or compute parameters indicative or predictive of heart failure (HF). Examples of HF parameter detectors 234 include an arrhythmia detector to detect arrhythmia parameters, a morphology detector to detect morphological parameters, impedance circuitry to detect DC impedance (e.g., transthoracic impedance), activity sensor to detect activity variance, posture sensors to sense posture or patient position, exercise compliance monitor to evaluate exercise compliance, heart rate detectors to detect heart rate and heart rate variability, pressure sensors to detect pressure, and so forth. It is noted that these detectors are examples, and others may be employed. Essentially, the microcontroller 220 may implement any detector that produces a parameter that may be used alone or in combination with another to predict or diagnose heart failure.

The HF parameters are stored in memory 236, which is coupled to the microcontroller 220 via a suitable data/address bus 238. In addition to these parameters, the memory 236 stores programmable operating parameters used by the microcontroller 220 to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

Microcontroller 220 also implements a parameter change sub-system 240 that evaluates the multiple HF diagnostic parameters collected by the HF parameter detectors 234. The parameter change sub-system can derive trends of individual parameters suggestive of changes to the patient's cardiac health. The results of the parameter change sub-system analysis can provide more meaningful information to the physicians or clinicians. For example, the analysis can convey that the patient's cardiac condition related to one or more of the parameters is stable or that a change in the condition has occurred.

As the HF parameters are collected and stored, the parameter change sub-system 240 determines if a condition for each set of HF parameters has changed, essentially providing a series of diagnostic values computed over time. The series of diagnostic values are stored in memory 236 and a trend analysis may be applied to the series to determine whether the patient's heart condition is improving or deteriorating. Furthermore, if the trend of diagnostic values crosses a programmable threshold, the implantable device generates an alert to inform the clinician of a worsening condition.

The microcontroller 220 may further be programmed to prescribe one or more pacing therapies 242 in response to results from the parameter change sub-system 240. For example, if the parameter change sub-system 240 predicts that conditions are worsening and heart failure may be imminent, the microcontroller 220 may prescribe a pacing therapy that attempts to counteract the parameters suggesting a worsening condition.

The components 234, 240, and 242 may be implemented in hardware as part of the microcontroller 220, or as software/firmware instructions programmed into the device and executed on the microcontroller 220 during certain modes of operation. These components may further be implemented independent from the microcontroller 220. Although not shown, the microcontroller 220 may further include other dedicated circuitry and/or firmware/software components that assist in monitoring various conditions of the patient's heart and managing pacing therapies.

The implantable cardiac device 100 has atrial sensing circuits 244 and ventricular sensing circuits 246 to detect the presence of cardiac activity in each of the four chambers of the heart. The sensing circuits 244 and 246 may be selectively coupled to the right atrial lead 104, coronary sinus lead 106, and the right ventricular lead 108 through the switch 226. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

The implantable cardiac device 100 is further equipped with an analog-to-digital (A/D) data acquisition system 252 to sample cardiac signals across any pair of desired electrodes. The system 252 is coupled to the right atrial lead 104, the coronary sinus lead 106, and the right ventricular lead 108 through the switch 226. Cardiac signals received from the leads are supplied to the data acquisition system 252, which is configured to acquire intracardiac electrogram (IEGM) signals, convert the raw analog data into a digital signal, and store the digital signals for processing.

The data acquisition system 252 is coupled to the microcontroller 220, or other detection circuitry, to assist in detecting various parameters and events. For instance, the system 252 acquires the signals used by the HF parameter detectors 234 to detect parameters indicative or suggestive of heart failure. The data acquisition system 252 is further configured to detect an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The data acquired by the data acquisition system 252 is stored in memory 236 and can be subsequently transmitted to an external device 254. The external device 254 may be implemented in many ways, including as a programmer, a transtelephonic transceiver, or a diagnostic system analyzer. Additionally, the external device 254 may be representative of an intermediate communication device that receives information from the implantable device and relays the information to another device or system for evaluation. In this manner, the HF diagnostic parameters and/or the results of any parameter change sub-system analysis may be output to the external device 254 for further analysis or presentation to the clinician.

In one implementation, a telemetry circuit 260 facilitates communication between the implantable device 100 and the external device 254. During programming or data output, the telemetry circuit 260 establishes a communication link 262 with the external device 254. In addition to downloading data to the external device, operating parameters for the implantable device 100 may be non-invasively programmed into the memory 236 by transmission from the external device 254 over link 262 and through the telemetry circuit 260. The microcontroller 220 activates the telemetry circuit 260 with a control signal 264. The telemetry circuit 260 allows intracardiac electrograms and status information relating to the operation of the device 100 (as contained in the microcontroller 220 or memory 236) to be sent to the external device 254 through an established communication link 262.

The implantable device 100 may include magnet detection circuitry (not shown), coupled to the microcontroller 220, to detect when a magnet is placed over the device 100. A magnet may be used by a clinician to perform various test functions of the device 100 and/or to signal the microcontroller 220 that the external programmer 254 is in place to receive or transmit data to the microcontroller 220 through the telemetry circuit 260.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, $O_2$ saturation, evoked response, pH of blood, and so forth.

In the illustrated implementation, the physiological sensors 270 include sensors for detecting patient activity and respiration. Any sensor capable of sensing such conditions, either directly or indirectly, may be used. In particular, the physiological sensors 270 include an activity sensor 272 to detect patient movement. The activity sensor 272 may be implemented in many ways, including as a three-dimensional (3D) DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which is hereby incorporated by reference.

An exemplary physiological sensor used to detect respiratory conditions is a minute ventilation (MV) sensor 274. The MV sensor 274 senses minute ventilation, which is the total volume of air that moves into and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other respiration sensors that may be used in addition to, or instead of, the MV sensor 274 include an $O_2$ sensor that measures oxygen-related parameters, a sensor to measure respiration rate, and a sensor to measure tidal volume.

The activity and respiratory signals generated by the sensors 270 are passed to the microcontroller 220 for measurement by the HF parameter detectors 234. Such signals can be used to determine HF diagnostic parameters that may be used in evaluation of the patient's heart and possible heart failure. The parameter change sub-system 240 analyzes trends in the HF diagnostic parameters from the detectors 234 to produce results that may be used by a clinician as a proxy for whether the heart condition is worsening or improving. If a worsening condition is determined, the microcontroller 220 may prescribe a pacing therapy 242 and/or may generate an alert that the patient requires attention.

The implantable cardiac device 100 additionally includes a battery 276 to supply operating power to various components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also has a predictable discharge characteristic so that elective replacement time can be detected. As one example, the device 100 employs lithium/silver vanadium oxide batteries.

The implantable cardiac device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for many uses including determining shock thresholds; detecting when the device has been implanted; measuring stroke volume; and detecting the opening of heart valves; and so forth. The impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrodes may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5-10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Diagnostic System

In the above described implementation, the parameter change sub-system is implemented within the implantable cardiac device 100. In other implementations, the parameter change sub-system may be partially or fully implemented in computing devices external to the implantable device 100. For instance, the parameter change sub-system may be implemented in an external programmer or in diagnostic computers used by the physician to analyze parameters suggestive of heart failure. One such system implementation is described below.

Figure 3:
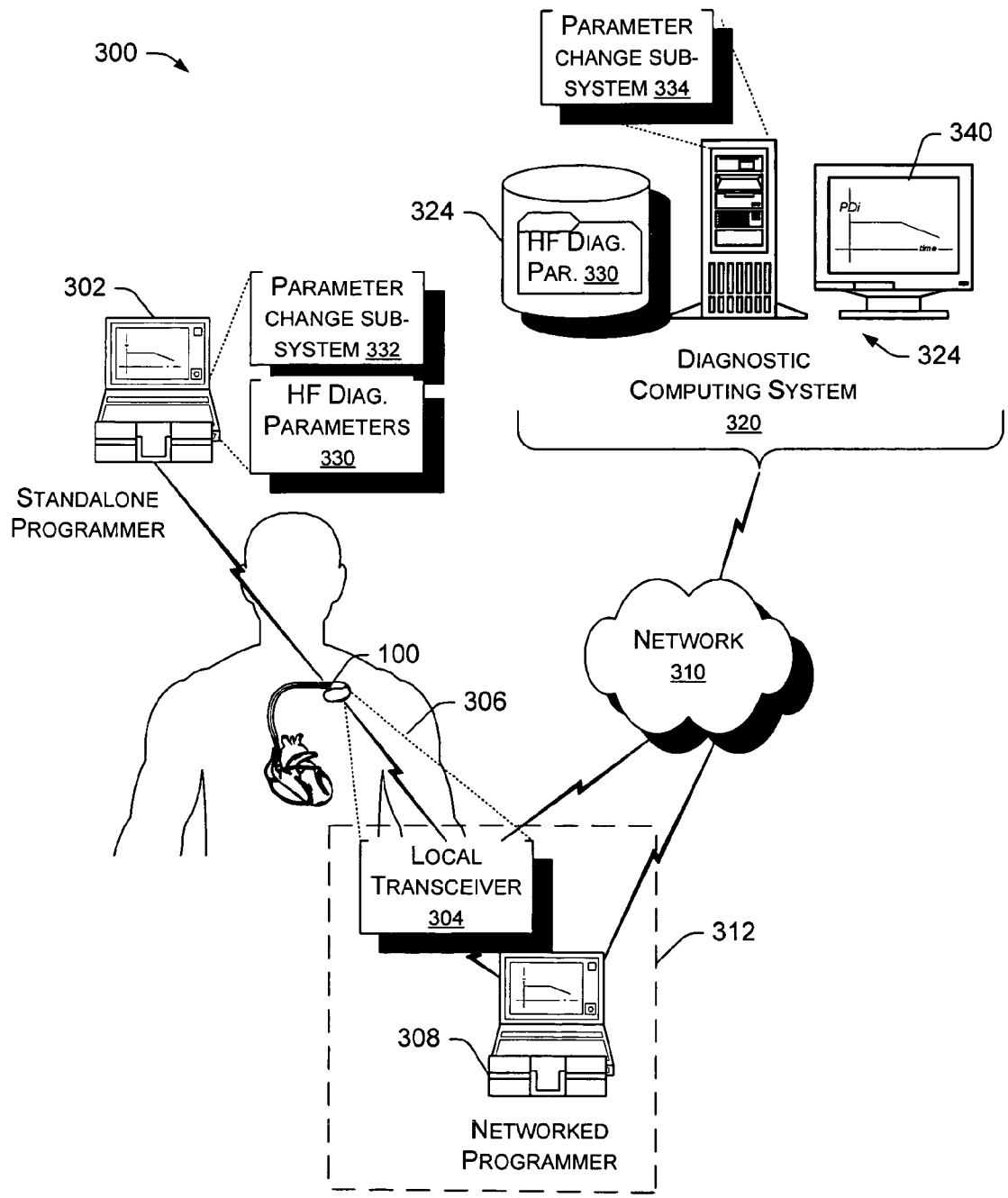
FIG. 3 is a diagrammatic illustration of a diagnostic system where the implantable cardiac device transmits data to one or more external devices for further processing.

FIG. 3 shows an HF diagnostic system 300 that includes the implantable cardiac device 100 in communication with one or more external devices that are capable of conducting diagnostics on data parameters received from the implantable device. The implantable device 100 measures and stores parameters overtime. Depending upon the size of the memory, the device may store parameters collected over many days or months. The parameters are then occasionally transmitted from the device 100 to one or more external devices. The data may be downloaded, for example, during physician checkups or other specified times. The external devices are configured with more processing and memory capabilities than the implantable device, and hence are able to conduct a more exhaustive analysis of the parameters.

The external devices may be implemented as a programmer, a computer, and/or a network of computing systems and data storages units. In this illustration, the implantable device 100 communicates with a standalone or offline programmer 302 via short-range telemetry technology. The offline programmer 302 is equipped with a wand that, when positioned proximal to the device 100, communicates with the device 100 through a magnetic coupling.

The implantable cardiac device 100 can alternatively, or additionally, be configured to communicate with a local transceiver 304 that is proximally located near the patient. The local transceiver 304 may be configured as an electronic communication device that is worn by the patient or is situated proximal to the patient, such as on a structure within the room or residence of the patient. The local transceiver 304 communicates with the implantable device 100 using short-range telemetry or longer-range high-frequency-based telemetry, such as RF (radio frequency) transmissions. Alternatively, the local transceiver 304 may be incorporated into the implantable device 100, as represented by dashed line 306. In this case, the device includes a separate and isolated package area that accommodates high-frequency transmissions without disrupting operation of the monitoring and stimulation circuitry.

The local transceiver 304 communicates with other external computing devices directly or via a network. In the illustrated implementation, the transceiver 304 transmits parameters received from the implantable device 100 to a networked programmer 308, which is connected to a network 310. The networked programmer 308 is similar in operation to standalone programmer 302, but differs in that it has a network port for connection to the network 310. The networked programmer 310 may be local to, or remote from, the local transceiver 304 depending upon the implementation and transmission range. Alternatively, the local transceiver 304 may be incorporated into the networked programmer 308, as represented by dashed line 312. Another possible implementation is for the local transceiver 304 to be connected directly to the network 310 for communication with remote computing devices and/or programmers including, for example, diagnostic computing system 320. Diagnostic computing system 320 includes one or more computers 322 for processing data received from the device 100 and a data store 324 for storing the device data.

The network 310 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 310 can be configured to support any number of different protocols, including HTTP (HyperText Transport Protocol), TCP/IP (Transmission Control Protocol/Internet Protocol), WAP (Wireless Application Protocol), Bluetooth, and so on.

The HF diagnostic parameters detected by the device 100 and offloaded to the external devices for further analysis are stored at the external devices. In FIG. 3, the HF diagnostic parameters 330 are shown stored in programmer 302 and the data store 324 of computing system 320.

The external devices are equipped with parameter change sub-systems to process the parameters received from the device 100, as well as any other parameters that might warrant consideration when diagnosing a patient's health (e.g., a patient's weight, age, etc.). In this example, the standalone programmer 302 implements parameter change sub-system 332 to analyze the HF diagnostic parameters 330 that are stored locally, and the diagnostic computer 322 implements parameter change sub-system 334 to analyze the HF diagnostic parameters 330 stored in data store 324.

The parameter change sub-system derives a trend for a parameter. The parameter change sub-system then determines whether the trend is continuing or if and when a trend change occurred. The parameter change sub-system can further diagnose a patient's cardiac health over time based at least in part upon the trend change. In some instances, the parameter change sub-system can further trigger an appropriate responsive action, such as a change in pacing therapy or administration of defibrillation shocking pulses.

Alternatively or additionally, the sub-system can present the results of the trend analysis to a care provider. The programmer 302 and/or computer 322 may present the results in a number of ways. One possibility is to present a user-perceptible image, such as a graphical user interface (UI), that depicts the parameter trend and points of inflection where that trend has changed. One example screen 340 is shown depicted on diagnostic computer 322. In this example, the screen 340 depicts a first trend and a trend change to a second different trend. More detailed examples are described below in greater detail in relation to FIGS. 6-11. The graphical UI assists the care provider in more quickly ascertaining the patient's cardiac condition.

Parameter Change Analysis

The parameter change sub-system implemented by the implantable cardiac device 100 or an external device (e.g., programmer 302 and/or computer 322) receives multiple HF diagnostic parameters detected by the device 100. The parameter change sub-system derives from the parameters one or more trends and/or trend changes. The parameter change sub-system uses the trends and/or trend changes to diagnose changes to the patient's heart condition.

One exemplary process by which the parameter change sub-system can derive parameter trends is described in more detail below in relation to FIGS. 4 and 5.

Generally, the sub-system identifies sub-sets of the parameter data to define a trend in the data. Each data sub-set that is consistent with an individual trend is graphically represented as a line segment of a given slope. The sub-system extrapolates the slope of the line, or existing trend, to subsequent data values. The extrapolated value for the subsequent data can then be compared to the actual measured value of the subsequent data. By comparing a difference between the extrapolated value and the measured value, the sub-system determines if the present trend continues in the subsequent data or if a trend change has occurred such that the subsequent data belongs to a new trend which is different from the existing trend.

The parameter change sub-system can be applied to complete sets of data to identify one or more trends in the data set. Alternatively, the parameter change sub-system may be applied to a real-time scenario where the sub-system analyzes samples as they are obtained and/or become available. For example, in one scenario, a history of a patient's parameter may be available from each of the last 30 days. The sub-system may process the available samples to derive one or more trends and to identify if and when a trend change occurred. Each subsequent day's sample can be processed as it becomes available to derive whether an existing trend is continuing or whether trend change has occurred.

In some implementations, the trend change analysis of an individual cardiac parameter can be accomplished with a trend change algorithm. The trend change algorithm serves to derive trends and trend changes. The trend change algorithm can identify sub-sets of the parameter's data which are consistent with a trend. The trend can be graphically represented as a line segment having a given slope as will be described below. The algorithm represents the line segment of the trend with the equation:

$$y(t) = p_i(t - t_{oi}) + y_{oi}$$

where $t_{oi}$ is time when the line segment begins;
$p_i$ is the slope of the line segment; and,
$y_{oi}$ is the ordinate at time $t_{oi}$.

For purposes of explanation, assume that at time $t_1$ a current trend is represented by the equation:

$$y(t) = p_1(t - t_{o1}) + y_{o1}$$

Subsequent data samples k occurring at time $t_1 + k\Delta t$ can then be analyzed, where k may be the next proceeding sampling event or a subsequent sampling event such that other sample events have occurred between $t_1$ and $k\Delta t$. The process extrapolates the existing slope to subsequent time $t_1 + k\Delta t$ with the equation:

$$y^*(t_1 + k\Delta t) = p1(t_1 + k\Delta t - t_{o1}) + y_{o1}$$

where y* stands for the extrapolated value of y. The measured value of y is represented by the equation:

$$y(t_1 + k\Delta t)$$

To determine if the existing trend continues to the subsequent sample event ($k\Delta t$), the process checks for a difference between the measured value and the extrapolated value. The difference is calculated with the equation:

$$e(t_1 + k\Delta t) = y(t_1 + k\Delta t) - y^*(t_1 + k\Delta t)$$

The process then takes the sum of the difference between the measured value and the extrapolated value at each sample period. This summation of the differences between the measured value and extrapolated value is referred to as the cumulative sum (CUMSUM). The CUMSUM calculated from time $t_1$ is:

$$\text{CUMSUM}(t_1 + k\Delta t) = \text{CUMSUM}(t_1 + (k-1)\Delta t) + e(t_1 + k\Delta t)$$

which equals the summation of e represented as:

$$\Sigma_{j=0 \text{ to } k} e(t_1 + j\Delta t)$$

To derive a trend change, the absolute value of the CUMSUM is compared, at each sampling time, to two thresholds TH1 and TH2, where TH1<TH2. If the absolute value of CUMSUM($t_1 + k\Delta t$) is less than or equal to a first threshold, TH1, the existing linear model continues to be acceptable, meaning that the existing trend is continuing. On the other hand, if the absolute value of CUMSUM($t_1 + k\Delta t$) is greater than the first threshold, TH1, the signal value $y(t_1 + k\Delta t)$ and corresponding time is stored as an abnormal value in a set of abnormal values.

Additionally, if the absolute value of CUMSUM($t_1 + k\Delta t$) is greater than the second threshold, TH2, the existing linear model is no longer acceptable and a new linear function is calculated, meaning that a new trend has begun. The new linear function can be calculated using the previously-stored set of abnormal values. Least square estimation is applied to the abnormal values. If three or more abnormal values comprise the set of abnormal values, they can be applied to the equation $y(t_1 + k\Delta t)$ such that:

$$TH1 < ABS(\text{CUMSUM}(t_1 + k\Delta t)) \leq TH2$$

Upon establishing a new linear function, the CUMSUM is reset to 0 so that the process can be repeated as data becomes available.

The thresholds TH1 and TH2 can be set to avoid abnormal artifacts that may arise in the data. Setting the thresholds higher, for example, might help avoid reading a trend change resulting from a spurious sample or two in an otherwise continuing trend.

Figure 4:
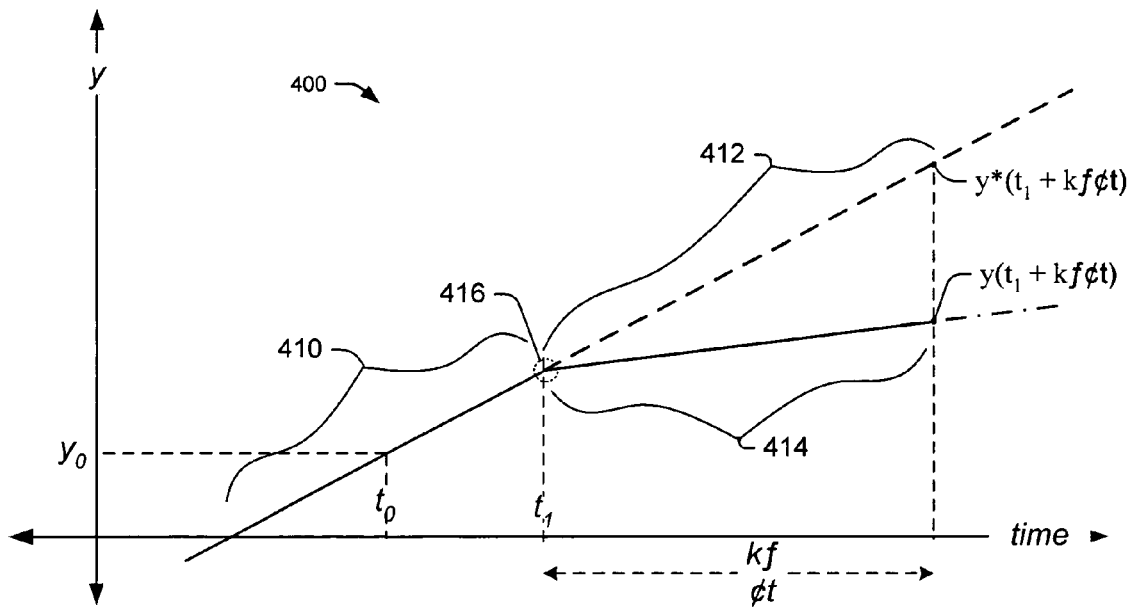
FIGS. 4-5 illustrate graphical representations of a parameter trend analysis implemented in the diagnostic system of FIG. 3.

FIG. 4 shows a graphical representation 400 of the parameter change algorithm when applied to a hypothetical cardiac parameter. A first linear function characterized by the equation $y(t) = p_1(t - t_{o1}) + y_{o1}$ is identified as a first line segment 410.

An extrapolated linear function referenced as line segment 412 is represented by the equation $y^*(t_1 + k\Delta t) = p1(t_1 + k\Delta t - t_{o1}) + y_{o1}$. A measured linear function referenced as line segment 414 is represented by the equation $y(t_1 + k\Delta t)$. The sum of the differences between extrapolated line segment 412 and measured line segment 414 is then determined via equation $e(t_1 + k\Delta t) = y(t_1 + k\Delta t) - y^*(t_1 + k\Delta t)$. The CUMSUM of the differences can be represented by the equation CUMSUM($t_1 + k\Delta t$) = CUMSUM($t_1 + (k-1)\Delta t$) + $e(t_1 + k\Delta t)$.

When the absolute value of CUMSUM($t_1 + k\Delta t$) exceeds a preset threshold (e.g., the second threshold TH2), the new trend represented by line segment 414 is confirmed. The process is then able to identify an inflection point 416 the represents a change in the trend. The process can further identify the time $t_1$ at which the trend change occurred.

Figure 5:
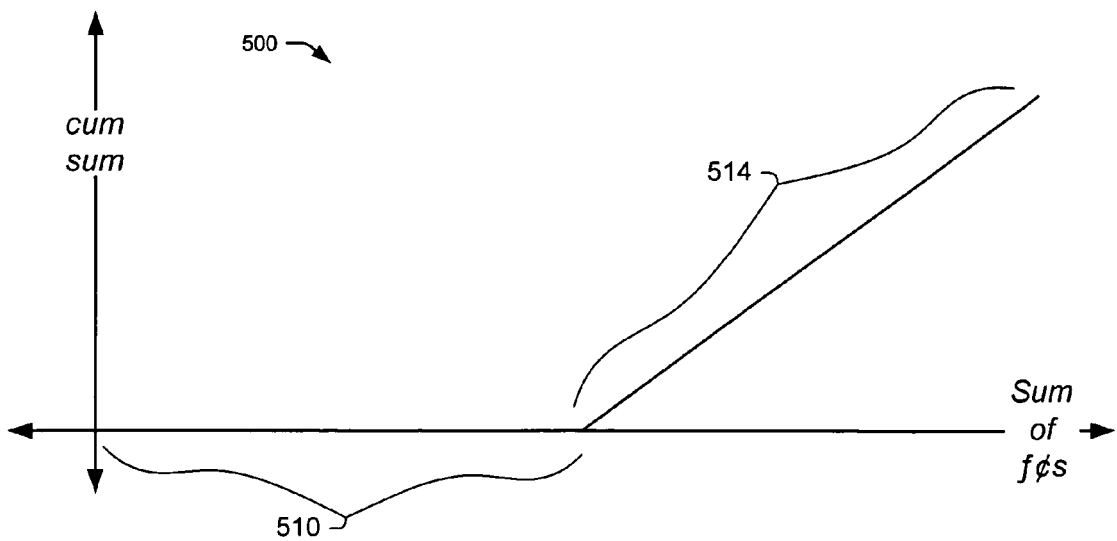

FIG. 5 illustrates a graphical representation 500 of the CUMSUM relative to the sum of the differences between the measured and extrapolated values illustrated in FIG. 4. A first region 510 generally corresponds to line segment 410 of FIG. 4, where an existing trend is generally in a steady state, where no significant difference exists between an extrapolated value and a measured value for the line segment 410. In contrast, a second region 514 generally corresponds to the divergence of measured line segment 414 from extrapolated line segment 412. In this instance, this divergence represents a trend change which began at inflection point 416 of FIG. 4. The trend represented by line segment 410 ends at inflection point 416 and a new trend represented by line segment 414 begins. A more detailed description of trend change algorithms can be found in an IEEE transaction on biomedical engineering, Vol 51, March 2004, Titled "On-line segmented algorithm for continuously monitored data in intensive care units" by Charbonnier et. al.

Examples of Derived Trend Change Analysis

Figure 6:
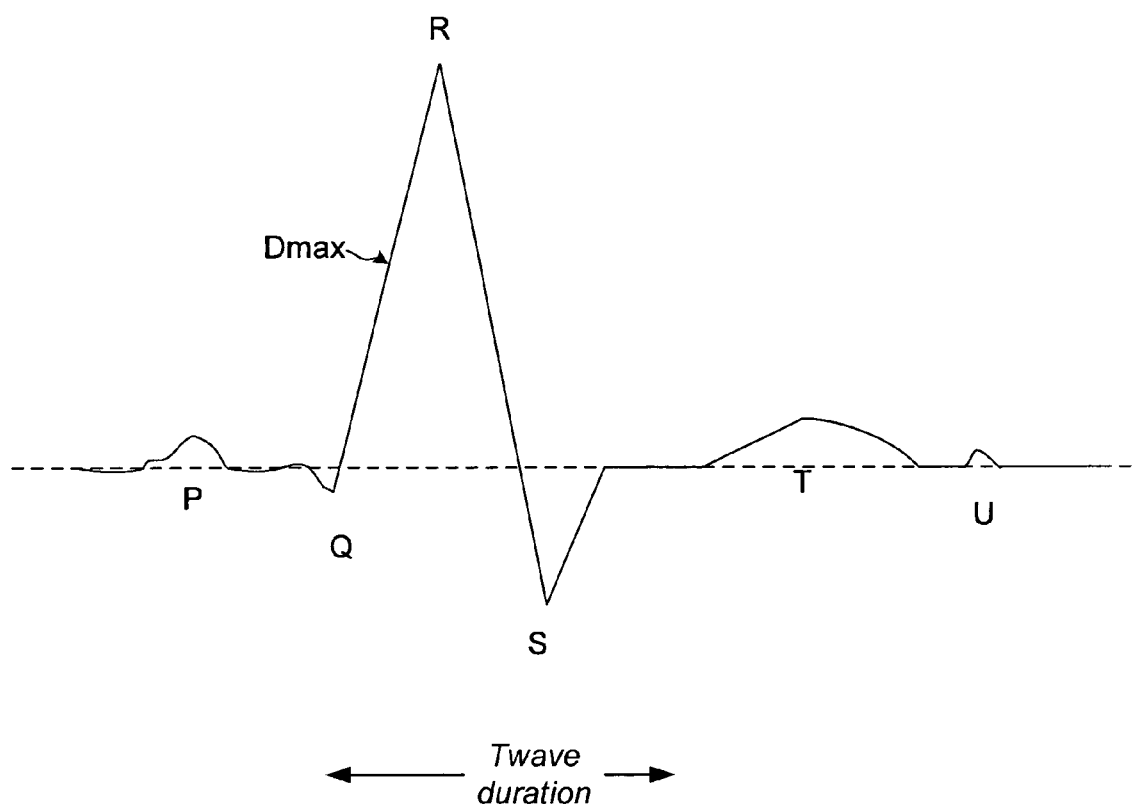
FIG. 6 illustrates a representation of an EKG for purposes of explanation of example cardiac parameters.

FIG. 6 illustrates a representation of a typical electrocardiogram (EKG) waveform including P, Q, R, S, T, and U waves. FIGS. 7-11 provide graphical examples of trend change analysis applied to some of the cardiac parameters associated with the EKG waveform.

EXAMPLE 1

Peak-to-Peak Slope (Dmax)

As shown in FIG. 6, peak-to-peak slope, or Dmax, is the measured value of the slope of the ascending transition from the Q wave to R wave of a patient's electrocardiogram.

Figure 7:
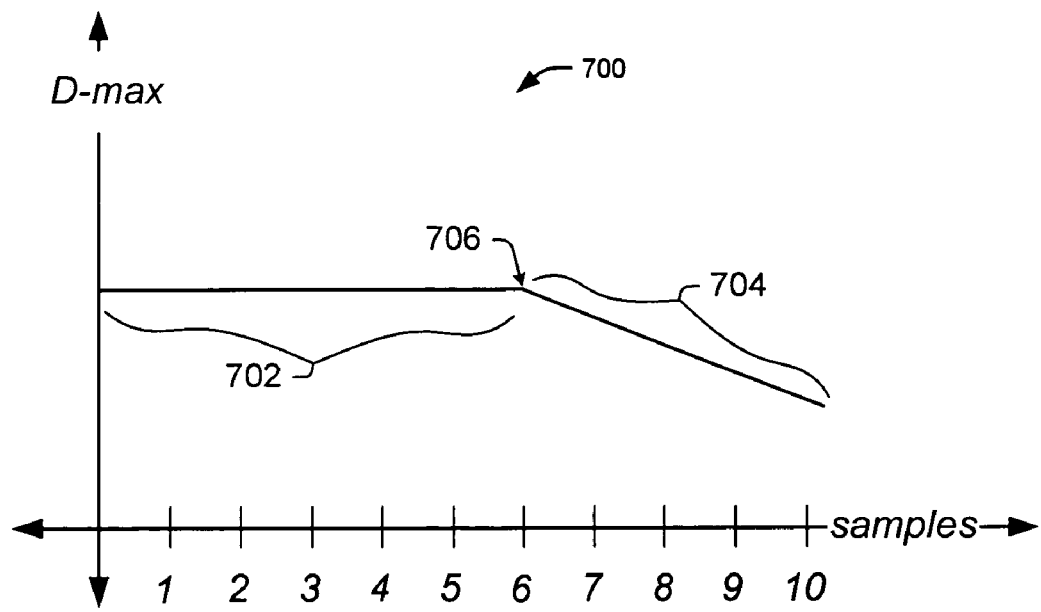
FIGS. 7-11 illustrate graphical representations of trend changes detected by the diagnostic system when parameter trend analysis is performed on various cardiac parameters.

FIG. 7 illustrates a graph 700 generated by the parameter change sub-system when processing the peak-to-peak slope (Dmax). The cardiac monitoring process described above in relation to FIGS. 1 and 2 can generate electrocardiograms from which Dmax can be derived by the microcontroller 220. The Dmax data is then passed to the device-resident parameter change sub-system 240 or exported from the device to external devices for analysis by parameter change sub-system 332 at programmer 302 and/or parameter change sub-system 334 at computer 322.

The graph 700 shows trends established by a set of Dmax data samples collected over time. The Dmax samples may be measured at various useful sampling periods. For example, the samples may be measured from consecutive heart beats, or taken over a period of days or months, or any other useful sampling period. For purposes of illustration, ten samples are shown in graph 700, although there is likely to be many more samples in practice.

In the Dmax graph 700, a first trend of Dmax is represented as a first line segment 702. The first trend continues for the first six data samples (1-6). A second different trend of Dmax is represented by a second line segment 704, which begins at data sample 7 and persists through sample 8-10.

The parameter change sub-system derives the first trend 702 and detects the change to the second trend 704. The sub-system further identifies an inflection or change point 706 where the first trend transitions to the second trend. This occurs approximately at sample 6.

The Dmax trend data can be used to diagnose changes to the patient's cardiac health. Further, the Dmax graph 700 can be presented via a graphical user interface to a care provider for him/her to quickly examine and ascertain whether the patient's cardiac health is progressing or deteriorating. In this example, a decreasing sloping of Dmax, as presented by the second trend 704, typifies a condition where the patient's heart is worsening. Accordingly, the care provider can quickly glean from the graph that this particular parameter is suggestive of a worsening heart condition.

The trend data can alternatively indicate that the patient's cardiac health is improving. If the Dmax trend change results in an upwardly sloped line segment 704 (rather than downwardly sloped as shown), the trend could be interpreted as an improving heart condition as the Dmax measurements are getting larger over time.

EXAMPLE 2

Paced Depolarization Integral (PDI)

Figure 8:
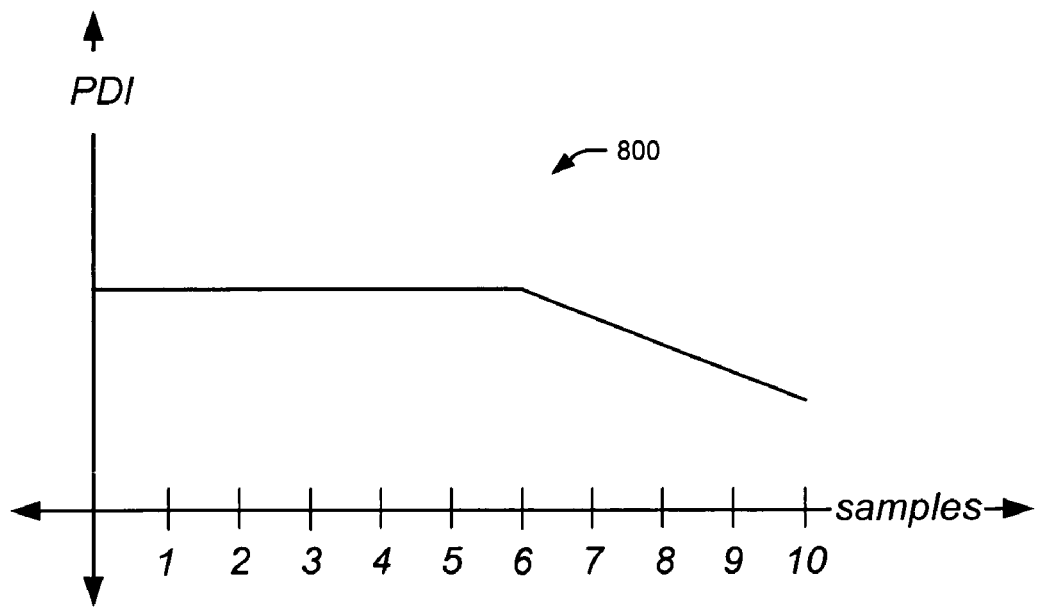

FIG. 8 illustrates a graph 800 generated by the parameter change sub-system when processing paced depolarization integral (PDI). PDI is the integration of the paced R-wave which yields a ventricular depolarization gradient. FIG. 8 illustrates a graphical representation of a first trend for PDI followed by a second different downwardly sloping trend, which may be suggestive of a worsening heart condition.

EXAMPLE 3

Thoracic Impedance

Figure 9:
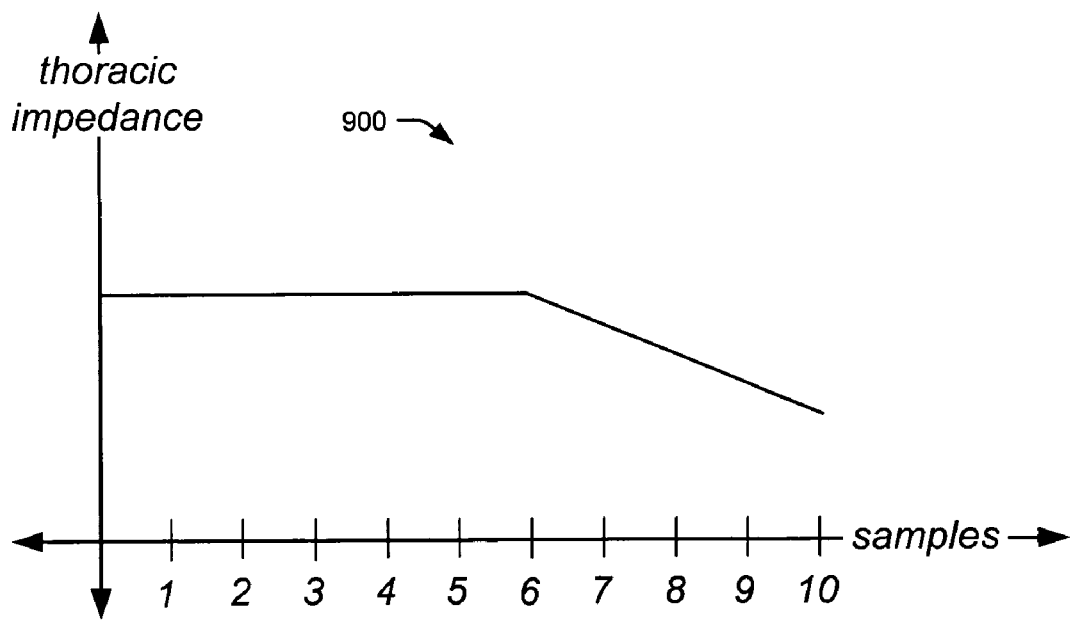

FIG. 9 illustrates a graph 900 generated by the parameter change sub-system when processing thoracic impedance. Thoracic impedance or transthoracic impedance is a measure of impedance across the chest cavity. Lungs filled with air have greater impedance than when empty. Thus, upon inhalation, impedance increases. FIG. 9 illustrates a graphical representation of a first trend for thoracic impedance followed by a second different downwardly sloping trend, which may be suggestive of a worsening heart condition.

EXAMPLE 4

T-Wave Duration

Figure 10:
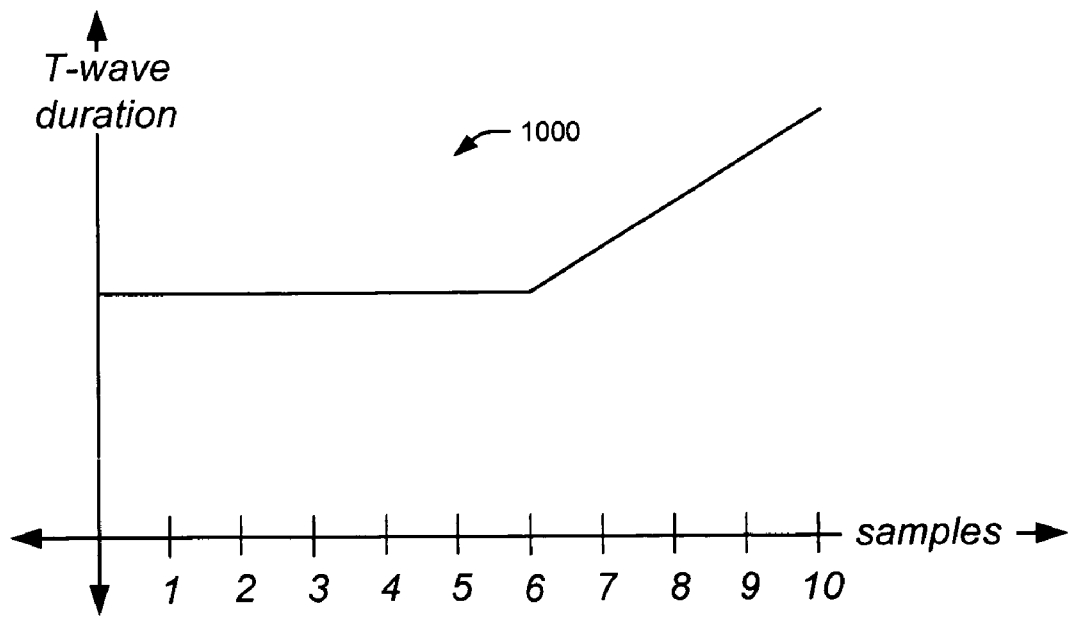

FIG. 10 illustrates a graph 1000 generated by the parameter change sub-system when processing T-wave duration. T-wave duration is the low frequency wave that follows an ST-segment on an EKG and represents repolarization of the ventricular myocardium. FIG. 10 illustrates a graphical representation of a first trend for thoracic impedance followed by a second different upwardly sloping trend. An increasing T-wave duration over time may be suggestive of a worsening heart condition.

EXAMPLE 5

Collective Parameter Analysis

Figure 11:
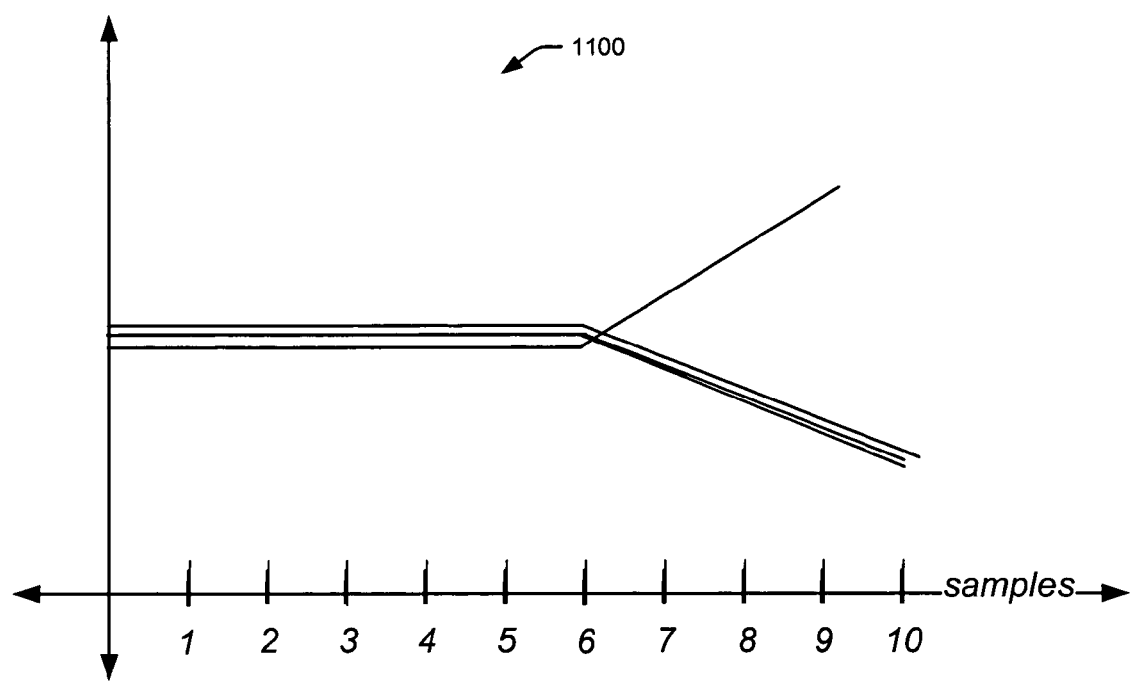

FIG. 11 illustrates a graph 1100 generated by the parameter change sub-system when processing the four heart related parameters of Dmax, PDI, thoracic impedance, and T-wave duration as described individually above in relation to FIGS. 7-10. in this particular instance, a trend change is detected for each of the four different heart related parameters at approximately the same sample time. A collective representation of trend data can be used to diagnose changes to the patient's cardiac health. The skilled artisan should recognize sets of individual parameters which may be advantageously combined for diagnostic purposes.

Operation

The implantable cardiac device 100 is implanted into a patient and over time begins to gather data that can be used as diagnostic parameters for heart failure. The data is stored on the device 100 and used in the parameter change processes resident on the device. Alternatively, the data can be communicated from the device 100 to an external computing device (e.g., programmers 302, 308 and computing system 320) for analysis.

Trend analysis may be applied to the data to determine whether a patient's heart condition is improving or worsening. The trend analysis may be performed on the implantable cardiac device 100, or on an external device, such as programmers 302, 308 or computing system 320, or on a combination of the implantable and external devices.

Figure 12:
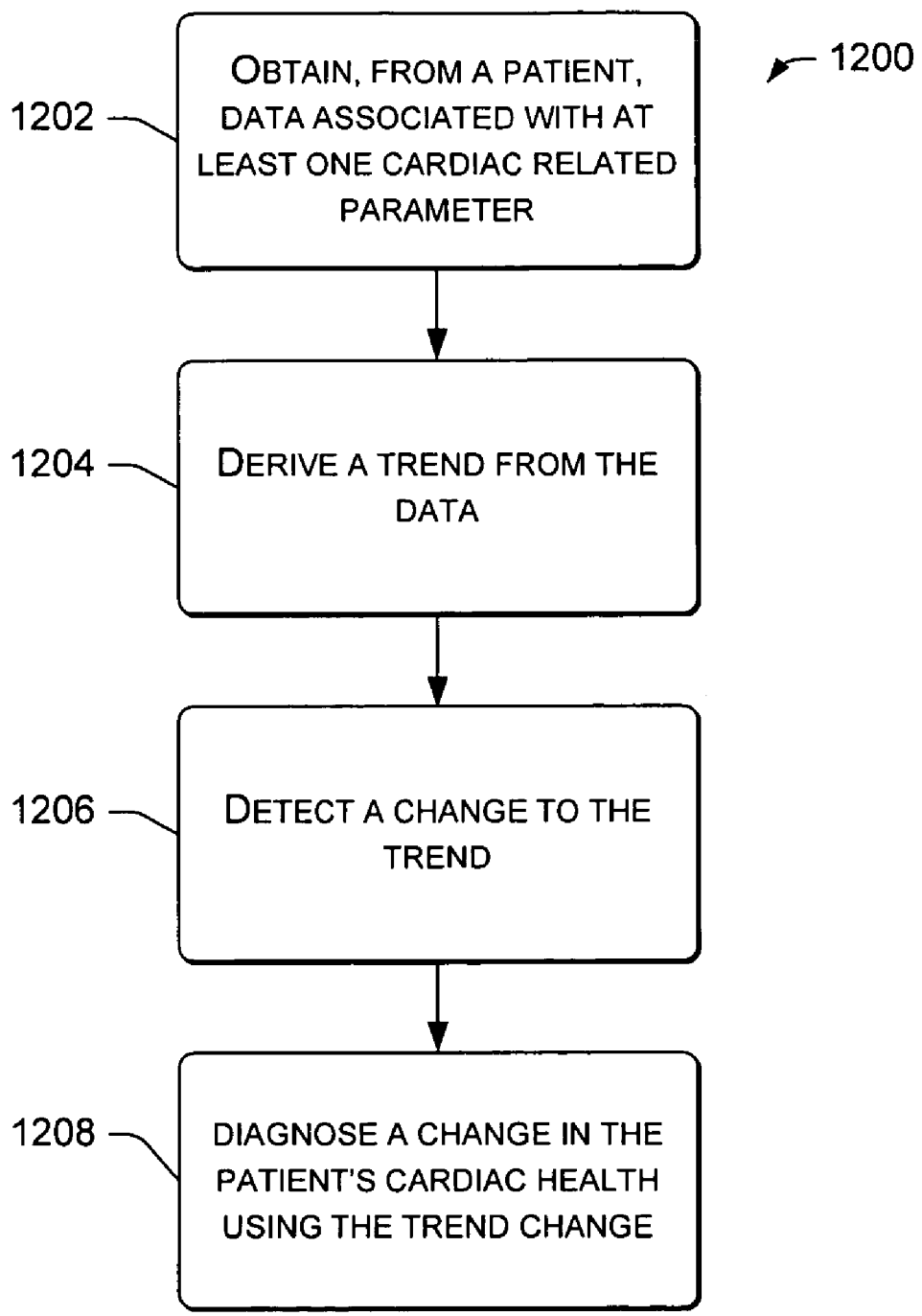
FIG. 12 is a flow diagram of an exemplary process for implementing the parameter trend analysis.

FIG. 12 shows a process 1200 for processing HF diagnostic parameters using parameter change analysis to diagnose a patient's condition regarding possible heart failure. In process 1200, the operations are summarized in individual blocks. The operations may be performed in hardware and/or as machine-readable instructions (software or firmware) that can be executed by a processor, such as the microcontroller used in the implantable device or the processing units at programmers 302, 308 and compute system 320.

At block 1202, the process obtains, from a patient, data associated with at least one cardiac-related parameter pertaining to the patient's cardiac health. The data includes data samples for HF diagnostic parameters collected over time by the implantable cardiac device. Possible HF diagnostic parameters include arrhythmia, morphology-related data, impedance, activity, activity variance, conduction delay, pressure, heart rate recovery, heart rate variability, minute ventilation, respiration, and intrinsic heart rate, and so forth. The data may further include data samples collected from other sources than the implantable cardiac device. Essentially any parameter that can be used in a diagnosis of heart failure may be considered in an analysis. For instance, in addition to parameters sensed and stored by the implantable device, externally input factors (e.g., a patient's weight, patient's age, etc.) may be included as parameters in the parameter change analysis for diagnosing the patient's heart function.

At block 1204, the process derives a trend from the data. In some implementations, the process derives the trend by establishing a first line segment from a first sub-set of the data relating to an individual parameter, whereby the first line segment represents a first trend of the parameter. One such technique is described above in relation to FIGS. 4-5. Examples of trends and trend changes of specific HF parameters are described above in relation to FIGS. 7-10, and a collective graph of trends of multiple HF parameters is described above in relation to FIG. 11.

At block 1206, the process detects a change to the trend. In some implementations, the process detects the change by determining a slope of the first line segment. The process then extrapolates the slope of the first line segment to a second sub-set of the data and establishes a second line segment from the second sub-set of the data. The process measures a measured slope of the second line segment, and compares the extrapolated slope to the measured slope.

The process then compares the extrapolated slope to the measured slope by determining a difference between them. If the difference is less than a first given value, the process treats the second line segment as continuing the first trend. If the difference is greater than the first given value and less than a second given value, then the process adds additional data representing additional sample times to the second sub-set and then repeats the above described acts of extrapolating, establishing, measuring and comparing. In an event that a difference between the extrapolated slope and measured slope is greater than the first given value and greater than the second given value then the process considers the second line segment to represent a second condition distinct from the first. One such technique is described above in relation to FIGS. 4-5.

At block 1208, the process uses the trend change to diagnose a change in the patient's cardiac health. In some implementations, the parameter trend changes are evaluated as an indicator of how the patient's cardiac health status is changing over time. For instance, over time, there may have been a parameter trend that indicated generally stable cardiac health. One or more of these parameters may have experienced trend change(s) indicative of worsening or improving cardiac health. The inflection point where the trend change occurs can also approximate the time that a change in cardiac health occurred. Several such individual examples are described above in relation to FIGS. 7-10. FIG. 11 describes an example which derives trend change in multiple parameters which are graphically represented superimposed over one another. While FIGS. 7-11 can indicate a worsening cardiac health, the trend change analysis can also indicate an improving cardiac health.

User Interface

The diagnostic system can be configured to allow observation of results from the trend change analysis.

Figure 13:
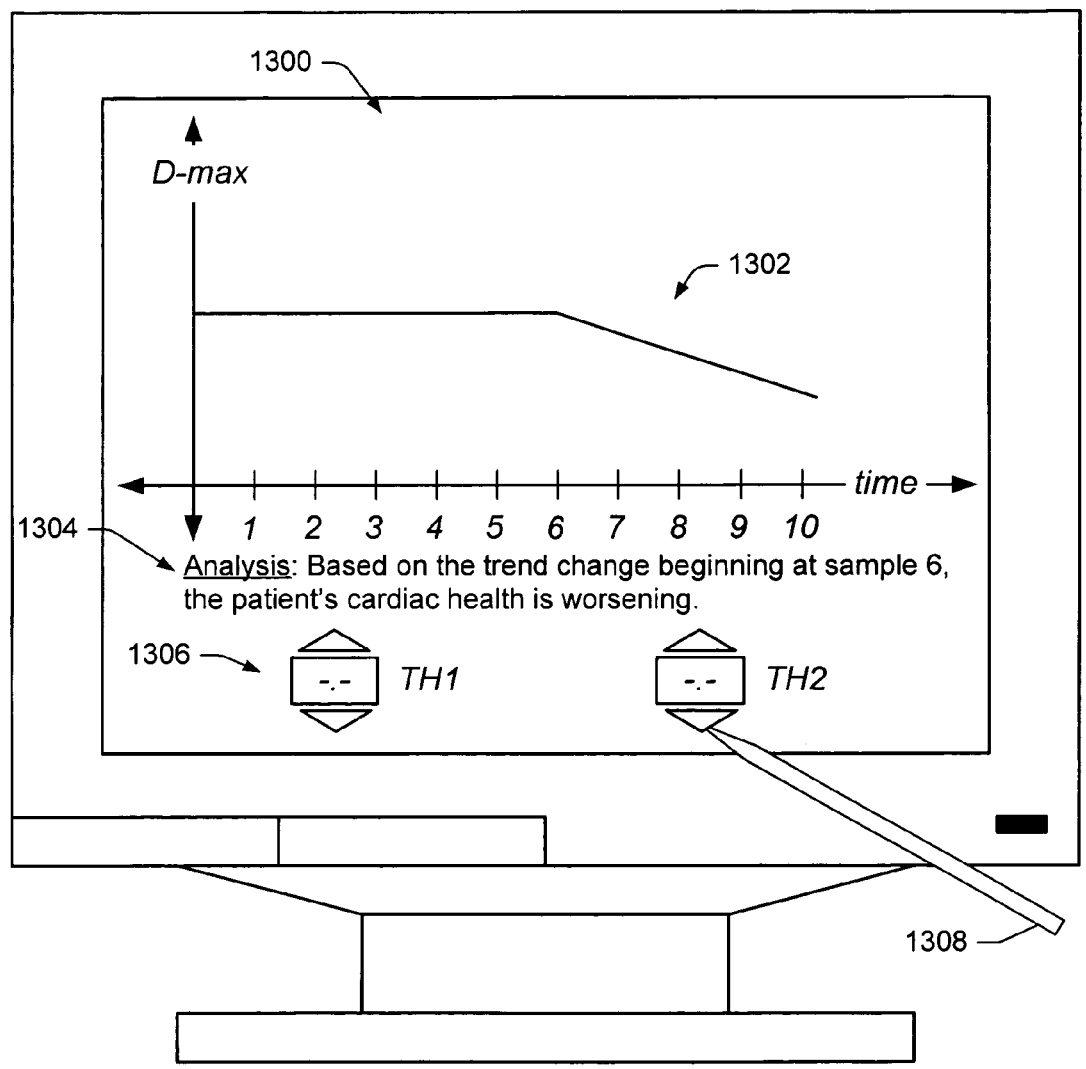
FIG. 13 illustrates a touch screen based graphical user interface to enable user observation of, and interaction with, the trend change analysis.

FIG. 13 illustrates one exemplary UI screen 1300 which presents a Dmax trend change graph at 1302. This Dmax trend change graph is described in more detail above in relation to FIG. 7. User interface 1300 also proposes one possible a patient diagnosis 1304 based upon the represented trend change. In this particular example, the diagnosis suggests that based upon the trend change, the patient's cardiac health may be worsening.

The user interface 1300 may also allow a physician to adjust a sensitivity level of the parameter change algorithm to reduce spurious trend change results. In this particular user-interface configuration, the TH1 and TH2 values utilized to derive the Dmax trend change graph 1302 are indicated on the user interface generally at 1306. The physician uses a stylus 1308 to adjust one or both of these values. The illustrated user interface is just one example, and many other configurations are possible.

CONCLUSION

The foregoing discussion describes techniques for diagnosing heart failure using trend change analysis. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:
1. A method comprising:
obtaining, from a patient, data associated with at least one cardiac-related parameter related to the patient's cardiac health, the data corresponding to numerous data samples obtained over first and second periods of time;
deriving a first trend of the parameter for the first period of time;

deriving an extrapolated trend, based on the first trend, for the second period of time;

deriving a second trend of the parameter during the second period of time;

processing the extrapolated trend and the second trend to determine whether the first trend continues for the second period or the second trend replaces the first trend for the second period; and diagnosing a change in the patient's cardiac health when the second trend replaces the first trend.

2. A method as recited in claim 1, wherein the obtaining comprises measuring the parameter using an implantable device.

3. A method as recited in claim 1, wherein the cardiac-related parameters are selected from a group of parameters comprising arrhythmia, morphology-related data, impedance, activity, activity variance, posture, conduction delay, pressure, heart rate recovery, heart rate variability, minute ventilation, respiration, and intrinsic heart rate.

4. A method as recited in claim 1, wherein deriving the first trend comprises establishing a first line segment from a first sub-set of the data corresponding to the first period of time and relating to an individual parameter, the first line segment representing the first trend of the parameter.

5. The method of claim 4, wherein deriving an extrapolated trend comprises extending the first line segment through the second period of time.

6. The method of claim 5, wherein deriving a second trend comprises establishing a second line segment from a second sub-set of the data corresponding to the second period of time and relating to the individual parameter.

7. The method of claim 6, wherein processing comprises comparing the extended first line segment and the second line segment.

8. A system comprising:
an implantable cardiac device to sense a parameter related to a patient's cardiac health; and
a parameter change detection sub-system configured to derive a first trend of the parameter for a first period of time, derive an extrapolated trend of the parameter for a subsequent period of time, wherein the extrapolated trend is based on the first trend, derive a second trend of the parameter for the subsequent period of time, process the extrapolated trend and the second trend to determine whether the first trend continues for the subsequent period or the second trend replaces the first trend for the subsequent period.

9. A system as recited in claim 8, wherein the parameter is selected from a group of heart-related parameters comprising arrhythmia, morphology-related data, impedance, activity, activity variance, conduction delay, pressure, heart rate recovery, heart rate variability, minute ventilation, respiration, and intrinsic heart rate.

10. A system as recited in claim 8, wherein the parameter change sub-system is configured as part of the implantable cardiac device.

11. A system as recited in claim 8, wherein the parameter change sub-system is configured in an external device which is separate from the implantable cardiac device.

12. A system as recited in claim 8, wherein the parameter change sub-system employs a line segmentation algorithm.

13. A system as recited in claim 8, wherein the parameter change sub-system is configured to generate a first line segment representative of the first trend and when the second trend replaces the first trend, to generate a second line segment representative of the second trend.

14. A system as recited in claim 8, wherein the parameter change sub-system is adjustable to distinguish artifacts from the trend.

15. An implantable cardiac device comprising:
a memory to store at least one heart-related parameter from a patient over a first period of time and a second period of time;
a processing unit to process the parameter using a parameter change algorithm to derive a first trend of the parameter for the first period of time, derive an extrapolated trend of the parameter for the second period of time, wherein the extrapolated trend is based on the first trend, derive a second trend of the parameter for the second period of time, process the extrapolated trend and the second trend to determine whether the first trend continues for the second period or the second trend replaces the first trend for the second period.

16. An implantable cardiac device as recited in claim 15 further comprising circuitry, responsive to the processing unit, to apply a pacing therapy to stimulate a patient's heart, the circuitry modifying the pacing therapy based, at least in part, on whether the second trend replaces the first trend for the second period.

17. An implantable cardiac device as recited in claim 15, wherein the heart related parameters are selected from a group comprising arrhythmia, morphology-related data, impedance, activity, activity variance, posture, conduction delay, pressure, heart rate recovery, heart rate variability, minute ventilation, respiration, and intrinsic heart rate.

18. A system comprising:
storage means for storing a parameter related to a patient's cardiac health over a first period of time and a second period of time; and
means for detecting a trend change in the parameter as an indication of a change in the patient's cardiac health by deriving a first trend of the parameter for the first period of time, deriving an extrapolated trend of the parameter for the second period of time, wherein the extrapolated trend is based on the first trend, deriving a second trend of the parameter for the second period of time, processing the extrapolated trend and the second trend to determine whether the first trend continues for the second period or the second trend replaces the first trend for the second period.

19. A system as recited in claim 18, wherein the parameter is measured by an implantable cardiac device.

20. A system as recited in claim 18, wherein the storage means stores multiple parameters and the detecting means detects trend changes in the multiple parameters, and wherein at least one parameter is measured by an implantable cardiac device and another parameter is obtained independently of the implantable cardiac device.

21. A system as recited in claim 18, further comprising means for presenting the trend change and a possible interpretation of the change in the patient's cardiac health.

22. A system as recited in claim 18, further comprising pacing means for generating electrical stimulation pulses in response to the detecting means.

* * * * *